United States Patent [19]

Rajagopalan

[11] Patent Number: 5,330,737

[45] Date of Patent: Jul. 19, 1994

[54] NITROGEN-SULFUR LIGANDS AS OPIATE RECEPTOR DRUG MIMICS

[75] Inventor: Raghavan Rajagopalan, St. Louis County, Mo.

[73] Assignee: Mallinckrodt Medical, Inc., St. Louis, Mo.

[21] Appl. No.: 804,852

[22] Filed: Dec. 6, 1991

[51] Int. Cl.$^5$ .................... A61K 49/02; A61K 43/00; C07D 213/74; C07D 213/83
[52] U.S. Cl. .................... 424/1.65; 534/10; 534/14; 546/331; 546/334; 546/336; 546/337
[58] Field of Search .............. 424/1.1, 1.65; 534/10, 534/14, 12; 546/331, 334, 335, 336, 337

[56] References Cited

U.S. PATENT DOCUMENTS

| | | | |
|---|---|---|---|
| 2,751,389 | 6/1956 | Bersworth | 546/5 X |
| 4,963,682 | 10/1990 | Bodor | 424/1.1 X |
| 5,071,636 | 12/1991 | Yamauchi et al. | 424/1.1 |
| 5,202,451 | 4/1993 | Fritzberg et al. | 556/419 |
| 5,204,357 | 4/1993 | Henning et al. | 546/331 |

FOREIGN PATENT DOCUMENTS 329481 8/1989 European Pat. Off. .
344724 12/1989 European Pat. Off. .

OTHER PUBLICATIONS

Bryson et al., *Inorg. Chem.* vol. 29, "Protecting Group in the Preparation of Thiolate Complexes of technetium", pp. 2948-2951 (1990).
Kung, *Nucl. Med. Biol.*, vol. 17, No. 1, "Radiopharmaceuticals for CNS Receptor Imaging with SPECT", pp. 85-92 (1990).

*Primary Examiner*—Richard D. Lovering
*Assistant Examiner*—John M. Covert

*Attorney, Agent, or Firm*—Brian K. Stierwalt

[57] ABSTRACT

The present invention relates particularly to novel aminothiol ligands that are suitable for complexing with a radionuclide, such as Tc, Re, or Ga, and are useful as general imaging agents for diagnostic purposes. The ligands have the general formulae (I) and (II):

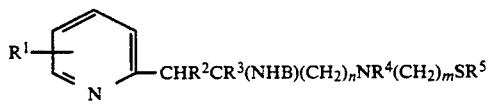

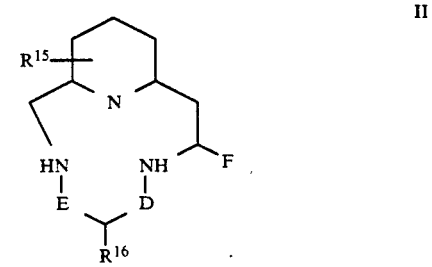

wherein for formula I, $R^1$-$R^4$, $R^6$, $R^7$ and $R^9$-$R^{14}$ can each be one of H, alkyl, aryl, hydroxyalkyl, alkoxycarbonyl, etc.; $R^5$ and $R^8$ are suitable sulfur protecting groups; m and n are 1-3; B can be one of $C(O)CHR^6CHR^7SR^8$, $CHR^9CHR^{10}C(O)NHR^{11}$, or $C(O)CHR^{12}CHR^{13}NHR^{14}$;

and wherein for formula II, $R^{15}$-$R^{18}$, $R^{20}$ and $R^{21}$ are defined in the same manner as $R^1$ above; D and E are either $C(O)$ or $CHR^{17}$; F is either $(CH_2)_dNR^{18}(CH_2)_eSR^{19}$ or $CHNR^{20}R^{21}(CH_2)_fSR^{22}$; $R^{19}$ and $R^{22}$ are defined in the same manner as $R^5$ above; d, e and f are 1-3.

17 Claims, No Drawings

NITROGEN-SULFUR LIGANDS AS OPIATE RECEPTOR DRUG MIMICS

BACKGROUND OF THE INVENTION

The present invention relates to novel ligands for forming radionuclide complexes, new complexes incorporating such ligands, processes for preparing such complexes, imaging agents incorporating such complexes, and methods of imaging using such imaging agents.

The use of radiographic imaging agents for visualizing skeletal structures, organs, or tissues, is well known in the area of biological and medical research and diagnostic procedures. The procedure whereby such imaging is accomplished, generally involves the preparation of radioactive agents, which, when introduced to the biological subject, are localized in the specific skeletal structures, organs or tissues to be studied. The localized radioactive agents may then be traced, plotted or scintiphotographed by radiation detectors, such as, traversing scanners or scintillation cameras. The distribution and relative intensity of the detected radioactive agents indicates the position of the tissue in which the agent is localized, and also shows the presence of aberrations, pathological conditions or the like.

In general, the radiographic imaging agents comprise radionuclide-labelled compounds; such as complexes of technetium 99m, rhenium 186 or rhenium 188, or other applicable radionuclides; with appropriate carriers, and auxiliary agents, such as delivery vehicles suitable for injection into, or aspiration by, the patient, physiological buffers and salts, and the like.

Novel aminothiol ligands, radiographic imaging agents, and methods or formulation and use have been previously described in co-pending U.S. patent application Ser. No. 07/584,314 now pending which is hereby incorporated by reference.

DETAILED DESCRIPTION OF THE INVENTION

The present invention relates particularly to novel aminothiol ligands that are suitable for complexing with a radionuclide, and are useful as general imaging agents for diagnostic purposes. In particular the present invention relates to novel ligands having the general formula (I) below:

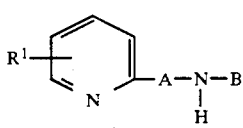

formula (I)

wherein $R^1$ is selected from the group consisting of hydrogen, alkyl, aryl, hydroxyalkyl, alkoxyl, mono- or poly- hydroxyalkyl, mono- or poly- alkoxyalkyl, acyl, alkoxycarbonyl, or carbamoyl; A is

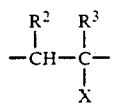

wherein $R^2$, and $R^3$ are defined in the same manner as $R^1$ above, and wherein X is

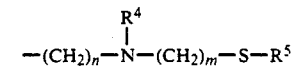

wherein n and m are 1 to 3, $R^4$ is defined in the same manner as $R^1$ above, and $R^5$ is a suitable protecting group selected from the group consisting of acetyl, benzoyl, alkoxycarbonyl, carbamoyl, methoxymethyl, and tetrahydropyranyl; and B is selected from the group consisting of

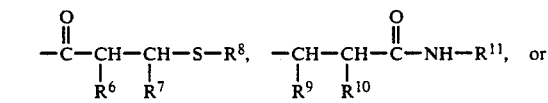

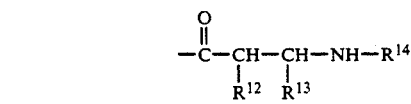

wherein $R^6$, $R^7$ and $R^9$ to $R^{14}$ are defined in the same manner as $R^1$ above, and $R^8$ is a suitable protecting group defined in the same manner as $R^5$ above.

In a preferred embodiment, ligands according to the present invention have the general formula (I) above, wherein $R^1$ is hydrogen or hydroxyl; A is

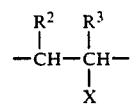

wherein $R^2$ and $R^3$ are each hydrogen, and X is

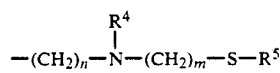

wherein $R^4$ is methyl, $R^5$ is benzoyl, n=1, and m=2; and B is

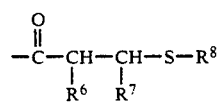

wherein $R^6$ and $R^7$ are each hydrogen, and $R^8$ is benzoyl.

The present invention also relates to novel ligands having the general formula (II) below:

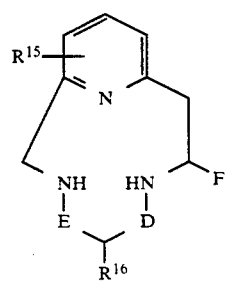

formula (II)

wherein $R^{15}$ and $R^{16}$ may be the same or different and are selected from the group consisting of hydrogen, alkyl, aryl, hydroxyalkyl, alkoxyl, mono- or poly- hydroxyalkyl, mono- or poly- alkoxyalkyl, acyl, alkoxycarbonyl, or carbamoyl; D and E may be the same or different and are selected from the group consisting of $$-C=O, \text{ or } -CH-R^{17}$$

wherein $R^{17}$ is defined in the same manner as $R^{15}$; and F is selected from the group consisting of

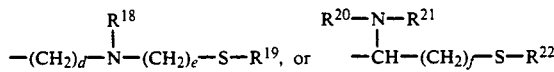

wherein $R^{18}$, $R^{20}$ and $R^{21}$ are defined in the same manner as $R^{15}$, $R^{19}$ and $R^{22}$ are suitable protecting groups selected from the group consisting of acetyl, benzoyl, alkoxycarbonyl, carbamoyl, methoxymethyl, and tetrahydropyranyl, and d, e, and f are 1 to 3.

In another preferred embodiment, ligands according to the present invention have the general formula (II) above, wherein $R^{15}$ is hydrogen, hydroxyl, or methoxyl; $R^{16}$ is hydrogen; F is $$-(CH_2)_d-\overset{R^{18}}{\underset{|}{N}}-(CH_2)_e-S-R^{19}$$

wherein $R^{18}$ is methyl, $R^{19}$ is benzoyl, d=1, and e=2; D is

—C=O;

and E is

—CH—R$^{17}$ wherein $R^{17}$ is hydrogen.

In a further preferred embodiment, ligands according to the present invention have the general formula (II) above, wherein $R^{15}$ is hydrogen, hydroxyl, or methoxyl; $R^{16}$ is hydrogen; F is $$-(CH_2)_d-\overset{R^{18}}{\underset{|}{N}}-(CH_2)_e-S-R^{19}$$

wherein $R^{18}$ is methyl, $R^{19}$ is benzoyl, d=1, and e=2; D is

—CH—R$^{17}$ wherein $R^{17}$ is hydrogen; and E is

—C=O.

In another preferred embodiment, ligands according to the present invention have the general formula (II) above, wherein $R^{15}$ is hydrogen; $R^{16}$ is hydrogen, hydroxyl, or methoxyl; F is $$-\overset{R^{20}-N-R^{21}}{\underset{|}{CH}}-(CH_2)_f-S-R^{22}$$

wherein $R^{20}$ and $R^{21}$ are methyl, $R^{22}$ is benzoyl, d=1, and e=2; D is

—C=O;

and E is

—CH—R$^{17}$ wherein $R^{17}$ is hydrogen.

In a still further preferred embodiment, ligands according to the present invention have the general formula (II) above, wherein $R^{15}$ is hydrogen; $R^{16}$ is hydrogen, hydroxyl, or methoxyl; F is $$-\overset{R^{20}-N-R^{21}}{\underset{|}{CH}}-(CH_2)_f-S-R^{22}$$

wherein $R^{20}$ and $R^{21}$ are methyl, $R^{22}$ is benzoyl, d=1, and e=2; D is

—CH—R$^{17}$ wherein $R^{17}$ is hydrogen; and E is

—C=O.

The novel ligands described above, may be incorporated into radionuclide complexes used as radiographic imaging agents. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium-99m complex forming reaction conditions. The solvent may then be removed by any appropriate means, such as evaporation. The complexes are then prepared for administration to the patient by dissolution or suspension in a pharmaceutically acceptable vehicle.

The ligands of the present invention may be prepared from commercially available starting materials such as 2-methylpyridine, 2-(2-aminoethyl)pyridine, 2-aminomethyl pyridine, homocysteinethiolactone, mercaptoethylamine, etc. by standard synthetic methods as described in the following Schemes 1 to 3, and in Examples 1.

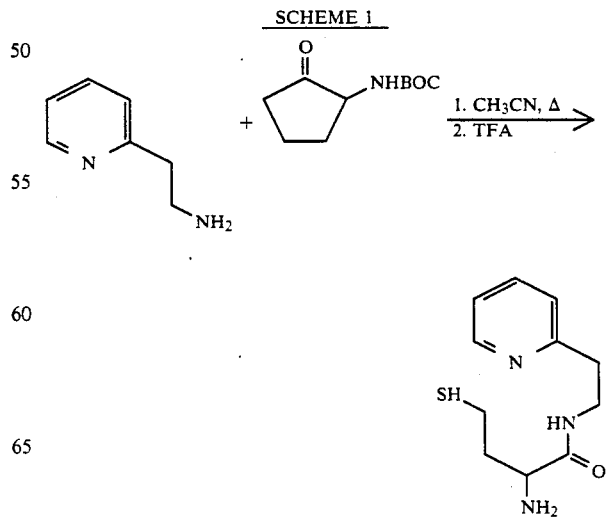

SCHEME 2
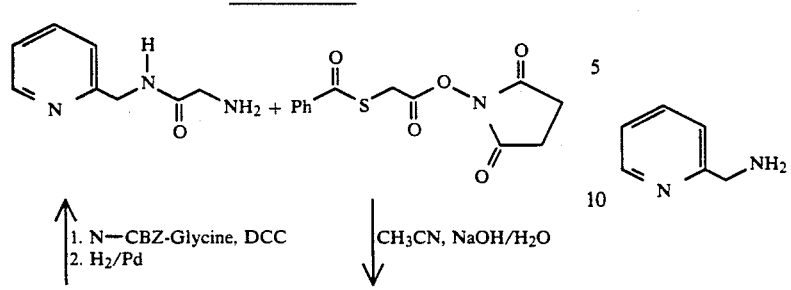
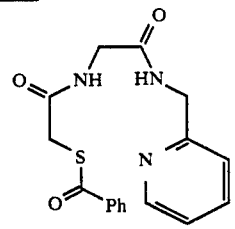
1. N—CBZ-Glycine, DCC
2. H₂/Pd
CH₃CN, NaOH/H₂O
-continued SCHEME 2
SCHEME 3
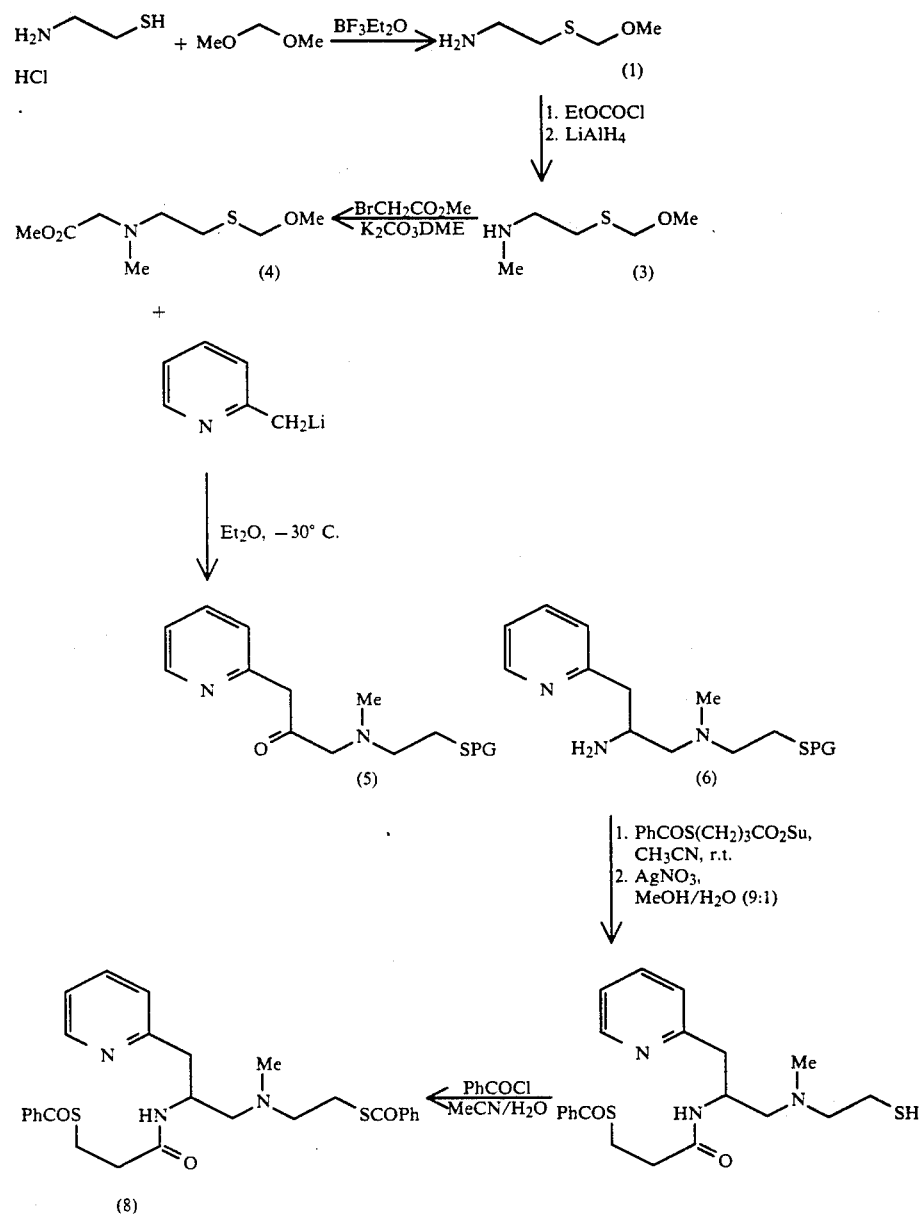
Radionuclide complexes according to the present invention may have the general formula (III) below:

formula (III)

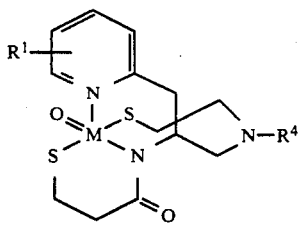

wherein M represents an appropriate radionuclide such as technetium, rhenium, or gallium; and $R^1$ and $R^4$ are as defined above in formula (I). In a preferred embodiment a radionuclide complex according to the present invention has the general formula (III) above, wherein $R^1$ is hydrogen or hydroxyl; and $R^4$ is methyl, benzyl, or cyclobutylmethyl.

Such a technetium radionuclide complex may be formed from a pertechnetate solution and a ligand having the general formula (I) above, wherein $R^1$ is hydrogen or hydroxyl; A is

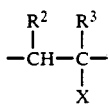

wherein $R^2$, and $R^3$ are each hydrogen; X is

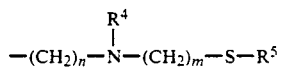

wherein $R^4$ is methyl, benzyl, or cyclobutylmethyl, $R^5$ is benzoyl, n=1, and m=2; and B is

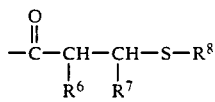

wherein $R^6$, and $R^7$ are each hydrogen, and $R^8$ is benzoyl.

Also, radionuclide complexes according to the present invention may have the general formula (IV) below:

formula (IV)

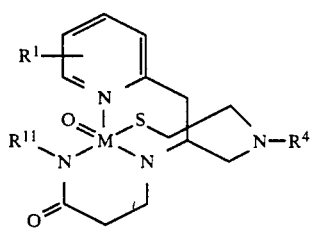

wherein M represents an appropriate radionuclide such as technetium, rhenium, or gallium; and $R^1$, $R^4$, and $R^{11}$ are as defined above in formula (I). In a preferred embodiment, a radionuclide complex according to the present invention has the general formula (IV) above, wherein $R^1$ is hydrogen or hydroxyl; and $R^4$ and $R^{11}$ are the same or different and are selected from the group consisting of methyl, benzyl, or cyclobutylmethyl.

Such a technetium radionuclide complex may be formed from a pertechnetate solution and a ligand having the general formula (I) above, wherein $R^1$ is hydrogen, or hydroxyl; A is

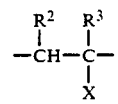

wherein $R^2$, and $R^3$ are each hydrogen, X is

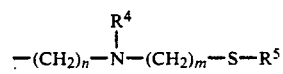

wherein $R^4$ is methyl, benzyl, or cyclobutylmethyl $R^5$ os benzoyl, n=1, and m=2; and B is

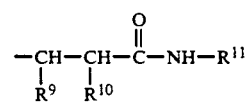

wherein $R^9$, and $R^{10}$ are each hydrogen, and $R^{11}$ is methyl.

Also, radionuclide complexes according to the present invention may have the general formula (V) below:

formula (V)

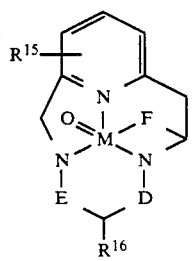

wherein M represents an appropriate radionuclide such as technetium, rhenium, or gallium; and D, E, F, $R^{15}$, and $R^{16}$ are as defined in formula (II) above. In a preferred embodiment, a technetium radionuclide complex having the general formula (V) may be formed from a pertechnetate solution and a ligand having the general formula (II) above, wherein $R^{15}$, and $R^{16}$ are hydrogen; D is

E is

wherein $R^{17}$ is hydrogen; and F is

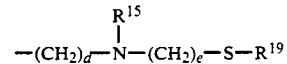

wherein $R^{18}$ is defined in the same manner as $R^{15}$ above, $R^{19}$ is benzoyl, d=1, and e=2.

The radionuclide containing solution may be obtained from radionuclide generators in a known manner. For example, when forming a technetium complex, the pertechnetate solution may be obtained from a technetium generator in a known manner. The radionuclide complex forming reaction is then carried out under appropriate reaction conditions. For example, the technetium 99m complex forming reaction is carried out under technetium complex forming temperatures, e.g. 20° C. to 100° C. for 10 minutes to several hours. A large excess of the appropriate ligands over the radionuclide complex forming amounts is preferably used. For example, when forming a technetium complex, at least a ten fold excess of the ligands over the pertechnetate solution is used. The pertechnetate is used in technetium complex forming amounts, e.g. about $10^6$ to $10^{12}$ molar amounts.

It is believed that certain radionuclide complexes of the present invention incorporating the ligands of the present invention have particular functional use as brain imaging agents. In particular, it is believed that these agents will act as opium alkaloid (e.g. morphine) mimics which may be selectively localized in the brain receptors, and may therefore exhibit optimal properties to function as diagnostic agents for the detection of brain disorders such as Alzheimer's disease, Parkinson's disease, narcotic addiction, etc.

A preferred complex for use in a brain imaging agent according to the present invention has the formula (VI) below:

formula (VI)

wherein $R^1$ is as defined above in formula (I). This complex may be formed by reaction of a pertechnetate solution with a ligand according to the present invention having the general formula (I) above, wherein $R^1$ is, in particular, hydrogen, hydroxyl, or methoxyl; A is

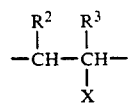

wherein $R^2$, and $R^3$ are each hydrogen, and X is

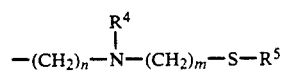

wherein $R^4$ is hydrogen, methyl, benzyl, or cyclobutylmethyl, $R^5$ is hydrogen, benzoyl, or methoxymethyl, n=1, and m=2; and B is

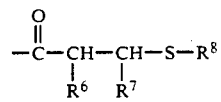

wherein $R^6$, and $R^7$ are each hydrogen, and $R^8$ is hydrogen or benzoyl.

A further preferred complex for use in a brain agent according to the present invention has the formula (VII) below:

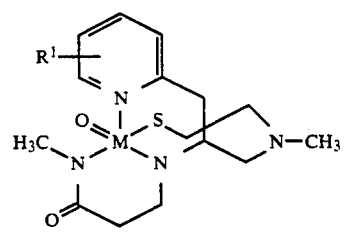

formula (VII)

wherein $R^1$ is as defined above in formula (I). This complex may be formed by reaction of a pertechnetate solution with a ligand having the general formula (I) above, wherein $R^1$ is, in particular, hydrogen, hydroxyl, or methoxyl; A is

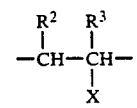

wherein $R^2$, and $R^3$ are each hydrogen, and X is

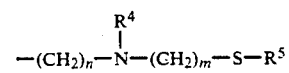

wherein $R^4$ is hydrogen, methyl, benzyl, or cyclobutylmethyl, $R^5$ is hydrogen, benzoyl, or methoxymethyl, n=1, and m=2; and B is

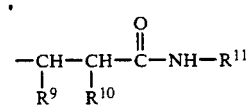

wherein $R^9$, and $R^{10}$ are each hydrogen, and $R^{11}$ is methyl.

A further preferred complex for use in a brain imaging agent according to the present invention has the formula (VIII) below:

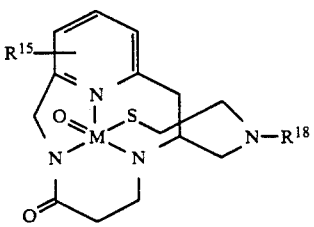

formula (VIII)

wherein M represents an appropriate radionuclide such as technetium, rhenium, or gallium; and $R^{15}$, and $R^{18}$ are as defined in formula (II) above. In a preferred embodiment, a brain agent according to the present invention has the general formula (VIII) above, wherein $R^{15}$ is hydrogen, hydroxyl, or methoxyl; and $R^{18}$ is hydrogen, methyl, benzyl, or cyclobutylmethyl. This complex may be formed by reaction of a pertechnetate solution with a ligand having the general formula (II) above, wherein $R^{15}$ is, in particular, hydrogen, hydroxyl, or methoxyl; $R^{16}$ is hydrogen; E is

—C=O;

D is

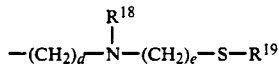

wherein $R^{17}$ is hydrogen; and F is $$-(CH_2)_d-\overset{R^{18}}{\underset{|}{N}}-(CH_2)_e-S-R^{19}$$

wherein $R^{18}$ is, in particular, hydrogen, methyl, benzyl, or cyclobutylmethyl, $R^{19}$ is hydrogen, benzoyl, or methoxymethyl, d=1, and e=2.

A further preferred complex for use in a brain imaging agent according to the present invention has the formula (IX) below:

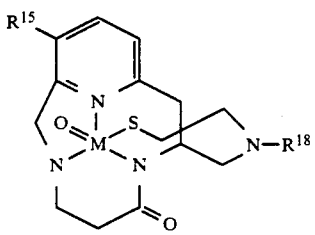

formula (IX)

wherein M represents an appropriate radionuclide such as technetium, rhenium, or gallium; and $R^{15}$, and $R^{18}$ are as defined in formula (II) above. In a further preferred embodiment, a brain agent according to the present invention has the general formula (IX) above, wherein $R^{15}$ is hydrogen, hydroxyl, or methoxyl; and $R^{18}$ is hydrogen, methyl, benzyl, or cyclobutylmethyl. This complex may be formed by reaction of a pertechnetate solution with a ligand having the general formula (II) above, wherein $R^{15}$ is, in particular, hydrogen, hydroxyl, or methoxyl; $R^{16}$ is hydrogen; D is

—C=O;

E is

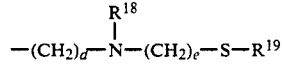

wherein $R^{17}$ is hydrogen; and F is $$-(CH_2)_d-\overset{R^{18}}{\underset{|}{N}}-(CH_2)_e-S-R^{19}$$

wherein $R^{18}$ is, in particular, hydrogen, methyl, benzyl, or cyclobutylmethyl, $R^{19}$ is hydrogen, benzoyl, or methoxymethyl, d=1, and e=2.

The present invention also relates to imaging agents containing a radionuclide complex as described above, in an amount sufficient for imaging, together with a pharmaceutically acceptable radiological vehicle. The radiological vehicle should be suitable for injection, such as human serum albumin; aqueous buffer solutions, e.g. tris(hydromethyl) aminomethane (and its salts), phosphate, citrate, bicarbonate, etc; sterile water; physiological saline; and balanced ionic solutions containing chloride salts, bicarbonate salts, or blood plasma cations, such as $Ca^{2+}$, $Na^+$, $K^+$, and $Mg^{2+}$.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 ml of aqueous solution may be prepared.

Imaging may be carried out in the normal manner, for example by injecting a sufficient amount of the imaging composition to provide adequate imaging and then scanning with a suitable machine, such as a gamma camera.

The complexes according to the present invention may be prepared in accordance with the example set forth below which relates to SCHEME 3 above.

EXAMPLE 1

Preparation of 1,9-Bis(S-benzoyl)mercapto-4,7-diaza-7-methyl-3-oxo-5-(2-pyridyl)methylnonane (8)

(a) 1-Amino-5-oxa-3-thiahexane (1). A suspension of mercaptoethylamine hydrochloride (113.5 g, 1.0 mol) in dimethoxymethane (450 mL) was treated with borontrifluoride etherate (25 mL, 0.2 mol) and stirred at ambient temperature for 4 hours. The fluffy white solid mass was cooled to 0° C. (ice-salt bath) and was carefully treated with ice-cold aqueous potassium hydroxide (100 g in 200 mL of water). The organic phase (top layer) was separated and the bottom layer was diluted with water (1 L) and extracted with methylene chloride (4×200 mL). The organic fractions were combined, dried (Na$_2$SO$_4$), filtered and the filtrate was stripped off the solvent under reduced pressure. Vacuum distillation (0.2 Torr, 67°-70° C.) afforded 64 g (60%) of the amine (1) as a colorless oil: $^1$H NMR (300 MHz, CDCl$_3$) δ4.56 (s, 2H), 3.30 (s, 3H), 2.83 (t, 2H, J=6.3 Hz), 2.62 (t, 2H, J=6.3 Hz), 1.45 (s, 2H); $^{13}$C NMR (75 MHz, CDCl$_3$) δ75.5, 55.6, 41.6, 35.4; CIMS m/z 122 (M+1).

(b) 1-(N-Methoxycarbonyl)amino-5-oxa-3-thiahexane (2). Methylchloroformate (56.7 g, 0.6 mol) was added in portions over a ten minute period to a vigorously stirring mixture of the amine (1) (65.5 g, 0.5 mol) and sodium carbonate (159.0 g, 1.5 mol) in methylene chloride (400 mL) and water (600 mL). After the addition, the solution was stirred at ambient temperature for 4 hours. The organic layer was separated, dried (MgSO$_4$), filtered, and the filtrate was stripped off the solvent under reduced pressure. Vacuum distillation (0.2 Torr, 126°-128° C.) afforded 78 g (87%) of the urethane (2) as a colorless oil: $^1$H NMR (300 MHz, CDCl$_3$) δ4.54 (s, 2H), 3.58 (s, 3H), 3.31 (t, 2H, J=6.2 Hz), 3.28 (s, 3H), 2.66 (t, 2H, J=6.2 Hz); $^{13}$C NMR (75 MHz, CDCl$_3$) δ157.2, 75.7, 55.7, 51.8, 40.8, 31.8; CIMS m/z 180 (M+1).

(c) 1-(N-Methyl)amino-5-oxa-3-thiahexane (3). A solution of the urethane (2) (53.7 g, 0.30 mol) in anhydrous THF (50 mL) was added dropwise over a 20 minute period to a cold (ice-salt bath), stirring suspension of lithium aluminum hydride (12.8 g, 0.33 mol) in anhydrous THF (200 mL) under an atmosphere of argon. Within 5 minutes after the addition, a vigorous exothermic reaction ensued. After the exotherm had subsided (approximately 15 minutes), the reaction mixture was heated to reflux under argon atmosphere for 2 hours and stirred at ambient temperature for 16 hours. The reaction mixture was cooled in ice bath and was carefully quenched with dropwise addition of ice-cold water (25 mL). The grey suspension was then treated with anhydrous sodium sulfate (100 g), filtered, and the filtrate was stripped off the solvent under reduced pressure. Vacuum distillation (0.2 Torr, 62°-65° C.) afforded 38 g (94%) of the amine (3) as a colorless oil: $^1$H NMR (300 MHz, CDCl$_3$) δ4.57 (s, 2H), 3.28 (s, 3H), 2.73 (t, 2H, J=5.1 Hz), 2.71 (t, 2H, J=5.1 Hz), 2.38 (s, 3H), 1.48 (bs, 1H); $^{13}$C NMR (75 MHz, CDCl$_3$) δ75.5, 55.6,·51.0, 35.8, 31.0; CIMS m/z 136 (M+1).

(d) Methyl-3-aza-3-methyl-7-oxa-5-thiaoctanoate (4). Methyl bromoacetate (32.1 g, 0.21 mol) was added to a vigorously stirring suspension of the amine (3) (27.0 g, 0.20 mol), finely grounded anhydrous potassium carbonate (55.2 g, 0.40 mol), and sodium iodide (3.0 g, 0.02 mol) in dimethoxyethane (150 mL). The reaction mixture was then heated under reflux for 2 hours. The inorganic salts were filtered off and washed with dimethoxyethane (3×50 mL). The filtrate was taken to dryness under reduced pressure to give a reddish brown oil. Kugelrorh distillation (0.2 Torr, 102°-105° C. pot temperature) afforded 33.2 g (80%) of the ester (4) as a pale green oil: $^1$H NMR (300 MHz, CDCl$_3$) δ4.05 (s, 2H), 3.68 (s, 3H), 3.28 (s, 2H), 2.85 (m, 2H), 2.75 (m, 2H), 2.37 (s, 3H); $^{13}$C NMR (75 MHz, CDCl$_3$) δ171.5, 75.6, 57.9, 56.7, 55.5, 51.4, 41.8, 28.3; CIMS m/z 208 (M+1).

(e) 4-Aza-8-methoxy-4-methyl-2-oxo-7-thia-1-(2-pyridyl)-octane (5). A solution of 2-methylpyridine (6.14 g, 0.066 mol) in anhydrous ether (10 mL) was cooled to −78° C. (dry ice-acetone bath) under an atmosphere of argon and treated with a solution of 44 mL (0.066 mol) lithium diisopropylamide mono-tetrahydrofuran (Aldrich, 1.5M solution in heptane). The resulting bright red solution was stirred at −78° C. for about 5 minutes and was transferred via a cannula to a cold (−30° C.) stirring solution of the ester (4) (12.42 g, 0.06 mol) in anhydrous ether (50 mL). After the addition, the yellow solution was warmed to 0° C., stirred at this temperature for 45 minutes, diluted with ether (100 mL), and quenched with 1N HCl (80 mL). The organic layer was separated, washed with brine, dried (Na$_2$SO$_4$), filtered, and the filtrate taken to dryness under reduced pressure. The brown residue was chromatographed over silica gel (1 kg). Elution with chloroform/methanol (95:5) afforded 11 g (68%) of a light sensitive ketone (5) as a brown oil: $^1$H NMR (300 MHz, CDCl$_3$) δ8.47 (d, 1H), 7.57 (m, 1H), 7.18 (d, 1H), 7.10 (dd, 1H), 4.55 (s, 2H), 3.90 (s, 2H), 3.32 (s, 2H), 3.25 (s, 3H), 2.63 (m, 4H), 2.26 (s, 3H); $^{13}$C NMR (75 MHz, CDCl$_3$) δ206.5, 155.0, 149.7, 136.7, 124.4, 122.0, 75.6, 66.5, 57.4, 55.5, 49.5, 42.2, 28.3; CIMS m/z 269 (M+1).

(f) 2-Amino-4-aza-8-methoxy-4-methyl-a-(2-pyridyl)methyl-7-thiaoctane (6). A mixture of the ketone (5) (5.4 g, 0.02 mol), ammonium acetate (15.4 g, 0.2 mol), and sodium cyanoborohydride (1.14 g, 0.02 mol) in methanol (80 mL) was stirred at ambient temperature for about 18 hours. The solvent was removed by evaporation under reduced pressure and the dark brown residue was dissolved in methylene chloride (100 mL), washed with brine (50 mL), dried (Na$_2$SO$_4$), filtered, and the filtrate taken to dryness under reduced pressure. Kugelrorh distillation (0.1 Torr, 140°-145° C. pot temperature) afforded 2.7 g (50%) of the purified amine (6) as viscous yellow oil: $^1$H NMR (300 MHz, CDCl$_3$) δ8.42 (d, 1H), 7.50 (m, 1H), 7.12 (d, 1H), 7.05 (dd, 1H), 4.52 (dd, 2H), 3.35 (m, 1H), 3.22 (s, 3H), 3.05 (bs, 2H), 2.81 (dd, 1H), 2.60 (m, 4H), 2.27 (m, 2H), 2.17 (s, 3H); $^{13}$C NMR (75 MHz, CDCl$_3$) δ159.5, 149.4, 136.6, 124.1, 121.5, 75.6, 63.3, 57.7, 55.5, 48.7, 42.9, 42.1, 28.6; CIMS m/z 270 (M+1).

(g) 2-[N-(S-Benzoylmercapto)propionyl]amino-4-aza-8-methoxy-4-methyl-1-(2-pyridyl)methyl-7-thiaoctane (7). A mixture of the amine (6) (1.35 g, 5 mmol) and N-succinimido 3-(S-benzoyl)mercaptopropionate (1.53 g, 5 mmol) in acetonitrile (100 mL) was stirred at ambient temperature for 4 hours. The solvent was removed under reduced pressure and the residue was redissolved in methylene chloride. The solution was washed with water, dried (MgSO$_4$), filtered and the filtrate taken to dryness under reduced pressure. Chromatography over silica gel (50 g) using chloroform/methanol (9:1) as eluent afforded 1.5 g of (7) as a yellow gum: $^1$H NMR (300 MHz, CDCl$_3$) δ8.42 (d, 1H), 7.88 (d, 2H), 7.51 (m, 2H), 7.48 (m, 2H), 7.21 (m, 1H), 7.05(m, 2H), 4.55 (dd, 2H), 4.28 (m, 1H), 3.30 (m, 2H), 3.25 (s, 3H), 3.05 (m, 2H), 2.41–2.65 (m, 6H), 2.20 (s, 3H); $^{13}$C NMR (75 MHz, CDCl$_3$) δ192.3, 170.8, 159.2, 149.0, 137.1, 136.6, 133.5, 128.7, 127.3, 124.6, 75.5, 59.0, 57.7, 55.5, 47.8, 41.9, 39.1, 36.1, 28.5, 24.6; CIMS m/z 462 (M+1).

(h) 1,9-Bis(S-benzoyl)mercapto-4,7-diaza-7-methyl-3-oxo-5-(2-pyridyl)methylnonane (8). A solution of the fully protected ligand (7) (1.38 g, 3 mmol) in methanol (15 mL) was treated with a solution of silver nitrate (1.02 g, 6 mmol) in aqueous methanol (1:4, 10 mL) and the entire mixture was stirred at ambient temperature for 4 hours. This procedure selectively removed the hemithioacetal protecting group and left the thioester intact. The off-white solid was filtered, washed with methanol, and dried. It was resuspended in methanol (20 mL), stirred, and treated with H$_2$S gas for about 15 minutes. The dark solution was filtered through celite and the filtrate taken to dryness under reduced pressure. The residue was immediately dissolved in acetonitrile/water (1:1, 20 mL), treated with triethylamine (500 mg, 5 mmol), and cooled to 0° C. in ice bath. The mixture was then treated with benzoyl chloride (700 mg, 5 mmol) and stirred at ambient temperature for 4 hours. The reaction mixture was poured onto saturated bicarbonate solution (25 mL) and extracted with methylene chloride (3×25 mL). The organic layer was washed with brine, dried (MgSO$_4$), filtered, and the filtrate evaporated. The residue was chromatographed over silica gel (50 g) using chloroform/methanol (97:3) as eluent to yield 540 mg of the desired ligand (8) as a light-sensitive yellow gum: $^1$H NMR (300 MHz, CDCl$_3$) δ8.39 (m, 1H), 7.85 (m, 4H), 7.49 (m, 3H), 7.35 (m, 4H), 7.18 (d, 1H), 7.15 (m, 2H), 4.30 (m, 1H), 3.25 (t, 2H), 3.05 (m, 4H), 2.51 (t, 2H), 2.45–2.70 (m, 4H), 2.27 (s, 3H); $^{13}$C NMR (75 MHz, CDCl$_3$) δ192.2, 170.7, 159.1, 149.0, 137.1, 136.6, 133.5, 128.7, 127.3, 124.5, 121.6, 59.2, 56.8, 47.6, 42.0, 38.9, 36.1, 26.9, 24.5; CIMS m/z 522 (M+1).

The foregoing has been a discussion of the preferred embodiments of the present invention, but is not intended to limit the invention in any way. Rather, many modifications, variations and changes in detail may be made within the scope of the present invention.

What is claimed is:

1. A ligand useful in forming radionuclide complexes, said ligand having the general formula:

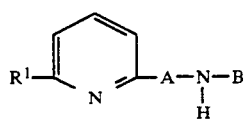

wherein $R^1$ is selected from the group consisting of hydrogen, hydroxyl, and lower alkoxyl; A is

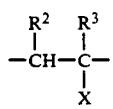

wherein $R^2$, and $R^3$ are defined in the same manner as $R^1$ above, and wherein X is

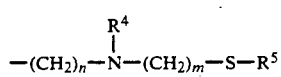

wherein n and m are 1 to 3, $R^4$ is selected from the group consisting of hydrogen, lower alkyl, benzyl, and cyclobutylmethyl, and $R^5$ is a suitable protecting group selected from the group consisting of acetyl, benzoyl, alkoxycarbonyl, carbamoyl, methoxymethyl, and tetrahydropyranyl; and B is selected from the group consisting of

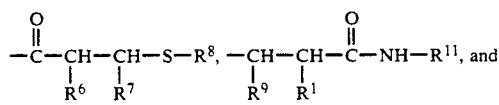

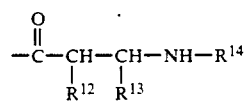

wherein $R^6$, $R^7$ and $R^9$ to $R^{14}$ are defined in the same manner as $R^1$ above, and $R^8$ is a suitable protecting group defined in the same manner as $R^5$ above.

2. A ligand according to claim 1, wherein $R^1$ is hydrogen or hydroxyl; A is

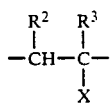

wherein $R^2$ and $R^3$ are each hydrogen, and X is

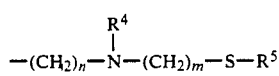

wherein $R^4$ is methyl, $R^5$ is benzoyl, n=1, and m=2; and B is

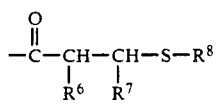

wherein $R^6$ and $R^7$ are each hydrogen, and $R^8$ is benzoyl.

3. A radionuclide complex having the general formula:

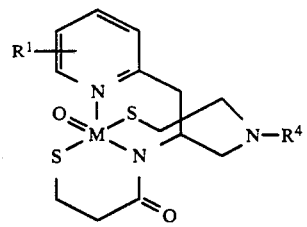

wherein M is a radionuclide; and wherein $R^1$ is hydrogen, hydroxyl, or methoxyl; and $R^4$ is hydrogen, methyl, benzyl, or cyclobutylmethyl.

4. A complex according to claim 3, wherein M is technetium, rhenium, or gallium.

5. A complex according to claim 3, wherein $R^1$ is hydrogen or hydroxyl; and $R^4$ is methyl, benzyl, or cyclobutylmethyl.

6. A complex according to claim 5, wherein $R^4$ is methyl.

7. A radionuclide complex having the general formula:

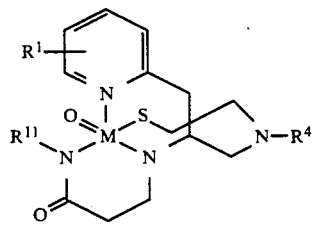

wherein M is a radionuclide; and wherein $R^1$ is hydrogen, hydroxyl, or methoxyl, and $R^4$ and $R^{11}$ may be the same or different and are selected from the group consisting of hydrogen, methyl, benzyl, and cyclobutylmethyl.

8. A complex according to claim 7, wherein M is technetium, rhenium, or gallium.

9. A complex according to claim 7, wherein $R^4$ and $R^{11}$ are each methyl.

10. A radiographic imaging agent comprising a complex having the general formula:

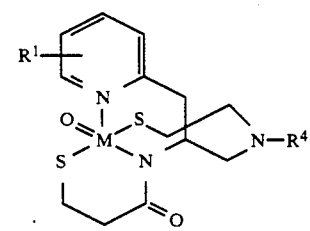

wherein M is a radionuclide; and wherein $R^1$ is hydrogen, hydroxyl, or methoxyl; and $R^4$ is hydrogen, methyl, benzyl, or cyclobutylmethyl; and a pharmaceutically acceptable radiological vehicle.

11. An imaging agent according to claim 10, wherein M is technetium, rhenium, or gallium.

12. An imaging agent according to claim 10, wherein said vehicle is suitable for injection or aspiration and is selected from the group consisting of human serum albumin, aqueous buffer solutions, sterile water, physiological saline, and balanced ionic solutions containing chloride salts, bicarbonate salts, or blood plasma cations.

13. An imaging agent according to claim 10, wherein the concentration of said complex in said vehicle is from about 1.0 to 50 millicuries.

14. A radiographic imaging agent comprising a complex having the general formula:

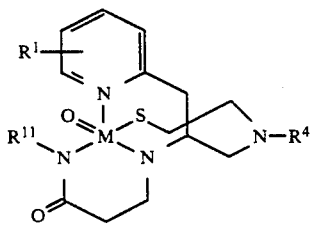

wherein M is a radionuclide; and wherein $R^1$ is hydrogen, hydroxyl, or methoxyl, and $R^4$ and $R^{11}$ may be the same or different and are selected from the group consisting of hydrogen, methyl, benzyl, and cyclobutylmethyl; and a pharmaceutically acceptable radiological vehicle.

15. An imaging agent according to claim 14, wherein M is technetium, rhenium, or gallium.

16. An imaging agent according to claim 14, wherein said vehicle is suitable for injection or aspiration and is selected from the group consisting of human serum albumin, aqueous buffer solutions, sterile water, physiological saline, and balanced ionic solutions containing chloride salts, bicarbonate salts, or blood plasma cations.

17. An imaging agent according to claim 14, wherein the concentration of said complex in said vehicle is from about 1.0 to 50 millicuries.

* * * * *